United States Patent
Sun et al.

(10) Patent No.: US 10,739,327 B2
(45) Date of Patent: Aug. 11, 2020

(54) APPARATUS AND METHOD FOR MONITORING THE QUALITY OF A LUBRICANT IN A COMPRESSOR

(71) Applicant: Danfoss (Tianjin) Ltd., Tianjin (CN)

(72) Inventors: Yingke Sun, Tianjin (CN); Dongdong Wang, Tianjin (CN); Leping Zhang, Tianjin (CN); Jingyuan Li, Tianjin (CN); Pierre Ginies, Tianjin (CN); Philippe Dewitte, Tianjin (CN); Liang Fan, Tianjin (CN)

(73) Assignee: DANFOSS (TIANJIN) LTD., Tianjin (CN)

( * ) Notice: Subject to any disclaimer, the term of this patent is extended or adjusted under 35 U.S.C. 154(b) by 297 days.

(21) Appl. No.: 15/571,940

(22) PCT Filed: May 5, 2016

(86) PCT No.: PCT/CN2016/081066
§ 371 (c)(1),
(2) Date: Mar. 29, 2018

(87) PCT Pub. No.: WO2016/180263
PCT Pub. Date: Nov. 17, 2016

(65) Prior Publication Data
US 2018/0202989 A1 Jul. 19, 2018

(30) Foreign Application Priority Data
May 8, 2015 (CN) .......................... 2015 1 0233934

(51) Int. Cl.
*G01N 33/30* (2006.01)
*F16N 19/00* (2006.01)
(Continued)

(52) U.S. Cl.
CPC ........... *G01N 33/30* (2013.01); *F16N 19/003* (2013.01); *F25B 31/002* (2013.01);
(Continued)

(58) Field of Classification Search
CPC .... G01F 23/268; G01F 23/266; G01F 23/263; G01F 23/265; G01F 23/0007;
(Continued)

(56) References Cited

U.S. PATENT DOCUMENTS 2,849,882 A * 9/1958 Lee ...................... G01F 23/263
73/304 C
3,182,255 A * 5/1965 Hopkins .............. G01N 27/223
324/666
(Continued)

FOREIGN PATENT DOCUMENTS

CN 101201344 A 6/2008
CN 101435788 A 5/2009
(Continued)

OTHER PUBLICATIONS

PCT Search Report for PCT Serial No. PCT/CN2016/081066 dated Aug. 11, 2016.

*Primary Examiner* — David A Rogers
(74) *Attorney, Agent, or Firm* — McCormick, Paulding & Huber PLLC

(57) ABSTRACT

Provided is a monitoring apparatus used to monitor lubricating oil inside a compressor. The monitoring apparatus comprises a first capacitance detector (100), a calculation unit, and a determining unit. The first capacitance detector (100) is disposed in a compressor (10) and is completely immersed in lubricating oil (20) inside the compressor (10), and is used to detect a first capacitance value (Cn). The calculation unit calculates a relative dielectric constant of the lubricating oil inside the compressor according to the
(Continued)

first capacitance value (Cn) detected by the first capacitance detector (100). The determining unit monitors, according to the calculated relative dielectric constant, whether quality of the lubricating oil (20) inside the compressor (10) encounters an exception. Further provided are a method for monitoring quality of lubricating oil inside a compressor and an apparatus and a method for monitoring a fluid level of lubricating oil inside a compressor. The monitoring apparatus and method may accurately monitors quality and a fluid level of lubricating oil inside a compressor, thereby reducing a monitoring cost and improving monitoring accuracy.

19 Claims, 4 Drawing Sheets

(51) Int. Cl.
F25B 31/00 (2006.01)
G01F 23/26 (2006.01)
G01N 27/22 (2006.01)
G01N 33/28 (2006.01)

(52) U.S. Cl.
CPC ......... G01F 23/265 (2013.01); G01N 27/221 (2013.01); G01N 33/2888 (2013.01); *G01N 33/2835* (2013.01)

(58) Field of Classification Search
CPC .. G01F 23/242; G01F 23/247; G01F 25/0061; G01N 33/2888; G01N 27/223; G01N 27/221; G01N 27/226; G01N 33/2847; G01N 22/04; G01N 33/03
See application file for complete search history.

(56) References Cited

U.S. PATENT DOCUMENTS

| | | | | |
|---|---|---|---|---|
| 3,226,635 A * | 12/1965 | Moe | .................. | G01N 22/04 324/667 |
| 4,080,593 A | 3/1978 | Gernandt et al. | | |
| 4,176,553 A * | 12/1979 | Wood | .................. | G01F 23/263 361/284 |
| 4,373,389 A * | 2/1983 | Decker | .................. | G01F 23/263 141/198 |
| 4,417,473 A * | 11/1983 | Tward | .................. | G01F 23/263 361/284 |
| 4,448,072 A * | 5/1984 | Tward | .................. | G01F 23/263 73/304 C |
| 4,490,988 A * | 1/1985 | Vogel | .................. | H02H 5/00 340/631 |
| 4,935,727 A * | 6/1990 | Re Fiorentin | ....... | G01F 23/0061 340/450 |
| 5,060,156 A * | 10/1991 | Vajgart | .................. | G06J 1/00 340/449 |
| 6,161,395 A * | 12/2000 | Okoren | .................. | F04B 39/0207 340/619 |
| 6,237,412 B1 * | 5/2001 | Morimoto | .................. | G01F 23/266 702/55 |
| 6,268,737 B1 * | 7/2001 | Marszalek | .................. | G01N 27/221 324/658 |
| 6,269,694 B2 * | 8/2001 | Morimoto | .................. | G01F 23/266 702/55 |
| 6,278,282 B1 * | 8/2001 | Marszalek | .................. | G01N 27/221 324/663 |
| 6,577,112 B2 * | 6/2003 | Lvovich | .................. | G01N 33/2888 324/71.1 |
| 6,590,402 B2 * | 7/2003 | Wang | .................. | G01N 27/06 324/663 |
| 6,847,216 B2 * | 1/2005 | Marszalek | .................. | G01N 33/2888 324/658 |
| 6,917,865 B2 * | 7/2005 | Arai | .................. | F01M 11/10 340/450.3 |
| 7,129,715 B2 * | 10/2006 | Hayashi | .................. | G01N 33/2888 324/685 |
| 7,523,646 B2 * | 4/2009 | Klun | .................. | G01N 33/03 210/85 |
| 7,729,870 B2 * | 6/2010 | Sun | .................. | G01F 23/265 324/441 |
| 8,161,814 B2 * | 4/2012 | Calcote | .................. | G01F 23/265 73/1.02 |
| 8,340,928 B2 * | 12/2012 | Sun | .................. | G01F 23/265 324/441 |
| 8,776,595 B2 * | 7/2014 | Milone | .................. | G01F 23/24 73/290 B |
| 9,518,855 B2 * | 12/2016 | Lee | .................. | G01F 23/265 |
| 10,025,323 B2 * | 7/2018 | Jang | .................. | G01F 23/0007 |
| 10,180,139 B2 * | 1/2019 | Brostrom | .................. | G01F 23/246 |
| 2001/0000851 A1 * | 5/2001 | Morimoto | .................. | G01F 23/266 73/304 C |
| 2004/0149032 A1 * | 8/2004 | Sell | .................. | G01F 23/263 73/304 C |
| 2007/0157718 A1 * | 7/2007 | Woodard | .................. | G01F 22/00 73/149 |
| 2009/0063060 A1 * | 3/2009 | Sun | .................. | G01F 23/265 702/52 |
| 2009/0120159 A1 * | 5/2009 | Barlesi | .................. | G01F 23/266 73/1.73 |
| 2009/0199635 A1 * | 8/2009 | Jacobson | .................. | G01F 23/268 73/304 C |
| 2010/0180663 A1 * | 7/2010 | Sun | .................. | G01F 23/265 73/1.02 |
| 2011/0120219 A1 * | 5/2011 | Barlesi | .................. | G01F 23/266 73/304 C |
| 2011/0239672 A1 * | 10/2011 | Won | .................. | F04B 39/0207 62/193 |
| 2016/0252092 A1 * | 9/2016 | Kulkarni | .................. | F04C 23/008 417/63 |
| 2016/0319816 A1 * | 11/2016 | Brostrom | .................. | F04B 39/0207 |

FOREIGN PATENT DOCUMENTS

| | | | | |
|---|---|---|---|---|
| CN | 103293201 A | | 9/2013 | |
| CN | 104165908 A | | 11/2014 | |
| CN | 104458521 A | | 3/2015 | |
| DE | 19711880 A1 | * | 10/1998 | ............ G07C 5/006 |
| DE | 10131106 A1 | * | 1/2003 | |
| DE | 10225716 A1 | * | 1/2004 | |
| DE | 102006027436 A1 | * | 12/2007 | |
| JP | S56101493 A | | 8/1981 | |
| WO | WO-2004109269 A1 | * | 12/2004 | ............ G01F 23/268 |

* cited by examiner

APPARATUS AND METHOD FOR MONITORING THE QUALITY OF A LUBRICANT IN A COMPRESSOR

CROSS-REFERENCE OF RELATED APPLICATION

This application is a National Stage application of International Patent Application No. PCT/CN2016/081066, filed on May 5, 2016, which claims priority to Chinese Patent Application No. 201510233934.4, filed on May 8, 2015, each of which is hereby incorporated by reference in its entirety.

TECHNICAL FIELD

The present invention relates to the technical field of detection, in particular to a monitoring apparatus and a monitoring method for monitoring lubricating oil in a compressor.

BACKGROUND

In some compressors, in order to reduce compressor wear and extend the service life of the compressor, a sufficient amount of lubricating oil is poured into the compressor, to provide adequate lubrication for the various components of the compressor. However, in actual applications, if the quality of the lubricating oil in a compressor deteriorates, this might result in failure of the lubricating function of the lubricating oil in the compressor.

Indices associated with the quality of lubricating oil in a compressor include the degree of dilution of the lubricating oil, foreign substance mixed into the lubricating oil, oxidation or carbonization of the lubricating oil, etc.

If the degree of dilution of lubricating oil in a compressor is too high, i.e. an excessive amount of coolant has mixed into the lubricating oil in the compressor, the concentration of the lubricating oil in the compressor will be too low as a result. This will cause a reduction in the viscosity of the lubricating oil; once the viscosity of the lubricating oil is reduced, serious wear to the bearings of the compressor will result. Thus, once the degree of dilution of lubricating oil is higher than a warning level, it is necessary to immediately stop the compressor or reduce the degree of dilution of the lubricating oil. In the prior art, some of the coolant that has mixed into the lubricating oil can generally be evaporated out by heating the lubricating oil, so as to reduce the degree of dilution of the lubricating oil.

If foreign substance, for instance iron fragments that have fallen off compressor bearings, becomes mixed into lubricating oil, this will aggravate wear of compressor components. Once iron fragments are mixed into lubricating oil, it is necessary to immediately stop the compressor, and remove the iron fragments from the lubricating oil.

If lubricating oil is oxidized or carbonized, the lubricating oil will lose its lubricating function, and this will lead to rapid wear of the compressor, shortening the service life of the compressor. Once lubricating oil is oxidized or carbonized, it is necessary to immediately stop the compressor, and replace the lubricating oil with new lubricating oil.

In summary, in order to ensure that a compressor can operate safely, the quality of lubricating oil in the compressor must be monitored on-line in real time.

Regarding the on-line real-time monitoring of the quality of lubricating oil in a compressor, in the prior art, the quality of lubricating oil is generally monitored by measuring the viscosity, density or contaminants of the lubricating oil. However, an existing monitoring apparatus for monitoring the quality of lubricating oil by measuring the viscosity, density or contaminants of the lubricating oil has a very high cost; the price of the monitoring apparatus is 400,000 to 1.6 million RMB. Furthermore, the installation of such an existing monitoring apparatus is very complex, and large amounts of data need to be processed, so the detection speed is slow. At present, such a monitoring apparatus is only suitable for laboratory tests; it cannot yet be used industrially.

SUMMARY

The objective of the present invention is to solve at least one aspect of the abovementioned problems and shortcomings in the prior art.

An objective of the present invention is to provide a monitoring apparatus and a monitoring method for on-line real-time monitoring of lubricating oil in a compressor, which can conveniently and accurately monitor quality, or quality and level, of the lubricating oil in the compressor.

According to one aspect of the present invention, a monitoring apparatus is provided, for monitoring lubricating oil in a compressor. The monitoring apparatus includes: a first capacitance detector, disposed in the compressor, and completely immersed in the lubricating oil in the compressor; a calculation unit, for calculating a relative dielectric constant $\varepsilon_r$ of the lubricating oil in the compressor according to a first capacitance value $C_{11}$ detected by the first capacitance detector; and a determining unit, for monitoring whether quality of the lubricating oil in the compressor is abnormal according to the relative dielectric constant $\varepsilon_r$ calculated.

According to an embodiment of the present invention, the monitoring apparatus further includes: a second capacitance detector, disposed vertically in the compressor. The calculation unit calculates, based on the calculated relative dielectric constant $\varepsilon_r$ of lubricating oil in the compressor and a second capacitance value $C_{21}$ detected by the second capacitance detector disposed vertically in the compressor, a depth H to which the second capacitance detector is immersed in the lubricating oil in the compressor; and the determining unit monitors, based on the depth H calculated, whether the level of lubricating oil in the compressor is lower than a safe level value.

According to another embodiment of the present invention, the relative dielectric constant $\varepsilon_r$ of the lubricating oil in the compressor is calculated according to formula (1):

$$\varepsilon_r = \frac{C_{11}}{C_{10}}, \tag{1}$$

wherein
$C_{10}$ is a capacitance value detected by the first capacitance detector in vacuum.

According to another embodiment of the present invention, the depth H to which the second capacitance detector is immersed in the lubricating oil is calculated according to formula (2):

$$H = \frac{L*(C_{21} - C_{20})}{(\varepsilon_r - 1)*C_{20}}, \tag{2}$$

wherein $C_{20}$ is a capacitance value detected by the second capacitance detector in air, and L is the length of the second capacitance detector in a vertical direction.

According to another embodiment of the present invention, the determining unit monitors whether the calculated relative dielectric constant $\varepsilon_r$ is greater than a predetermined dielectric constant value, and if the calculated relative dielectric constant $\varepsilon_r$ is greater than the predetermined dielectric constant value, the determining unit determines that the quality of the lubricating oil in the compressor is abnormal; and/or the determining unit monitors whether the calculated depth H is less than a predetermined depth value, and if the calculated depth H is less than the predetermined depth value, the determining unit determines that the level of lubricating oil in the compressor is lower than a safe level value.

According to another embodiment of the present invention, the first capacitance detector is a parallel-plate capacitance detector or a cylindrical capacitance detector; the second capacitance detector is a parallel-plate capacitance detector or a cylindrical capacitance detector.

According to another embodiment of the present invention, the first capacitance detector is substantially horizontally installed on a bottom wall of an oil tank in the compressor.

According to another embodiment of the present invention, the second capacitance detector is installed vertically on a sidewall of the oil tank in the compressor.

According to another practical embodiment of the present invention, a lower end of the second capacitance detector is in contact with a bottom wall of the oil tank in the compressor.

According to another embodiment of the present invention, the first capacitance detector and the second capacitance detector are two physically separated components or are integrated to form a one-piece component.

According to another aspect of the present invention, a monitoring method is provided, for monitoring lubricating oil in a compressor. The monitoring method includes steps of: calculating a relative dielectric constant $\varepsilon_r$ of lubricating oil in a compressor according to a first capacitance value $C_{11}$ detected by a first capacitance detector completely immersed in the compressor, and monitoring whether quality of the lubricating oil in the compressor is abnormal according to the relative dielectric constant $\varepsilon_r$ calculated.

According to an embodiment of the present invention, the abovementioned method further includes: calculating, based on a second capacitance value $C_{21}$ detected by a second capacitance detector disposed vertically in the compressor and the calculated relative dielectric constant $\varepsilon_r$ of lubricating oil in the compressor, a depth H to which the second capacitance detector is immersed in the lubricating oil in the compressor.

According to another embodiment of the present invention, in the abovementioned method, the relative dielectric constant $\varepsilon_r$ of the lubricating oil in the compressor is calculated according to formula (1):

$$\varepsilon_r = \frac{C_{11}}{C_{10}}, \tag{1}$$

wherein $C_{10}$ is a capacitance value detected by the first capacitance detector in vacuum.

According to another embodiment of the present invention, in the abovementioned method, the depth H to which the second capacitance detector is immersed in the lubricating oil is calculated according to formula (2):

$$H = \frac{L*(C_{21} - C_{20})}{(\varepsilon_r - 1)*C_{20}}, \tag{2}$$

wherein $C_{20}$ is a capacitance value detected by the second capacitance detector in air, and L is the length of the second capacitance detector in a vertical direction.

According to another embodiment of the present invention, in the abovementioned method, when the calculated relative dielectric constant $\varepsilon_r$ is greater than a predetermined dielectric constant value, the quality of lubricating oil in the compressor is determined as abnormal; and/or when the calculated depth H is less than a predetermined depth value, the level of the lubricating oil in the compressor is determined as lower than a safe level.

According to another embodiment of the present invention, the abovementioned method further includes: switching off the compressor when the calculated relative dielectric constant $\varepsilon_r$ is greater than a predetermined dielectric constant value or when the calculated depth H is less than a predetermined depth value.

According to another embodiment of the present invention, in the abovementioned method, the first capacitance detector is a parallel-plate capacitance detector or a cylindrical capacitance detector; the second capacitance detector is a parallel-plate capacitance detector or a cylindrical capacitance detector.

According to another embodiment of the present invention, in the abovementioned method, the first capacitance detector is substantially horizontally installed on a bottom wall of an oil tank in the compressor.

According to another embodiment of the present invention, in the abovementioned method, the second capacitance detector is installed vertically on a sidewall of the oil tank in the compressor.

According to another embodiment of the present invention, in the abovementioned method, a lower end of the second capacitance detector is in contact with a bottom wall of the oil tank in the compressor.

According to another embodiment of the present invention, in the abovementioned method, the first capacitance detector and the second capacitance detector are two physically separated components or are integrated to form a one-piece component.

In the monitoring apparatus and monitoring method in the various practical embodiments of the present invention above, the capacitance detectors enable convenient and accurate monitoring of the quality of lubricating oil in a compressor. Moreover, continuous real-time detection of the level of lubricating oil can be carried out to realize simultaneous detection of the quality and level of lubricating oil. The monitoring apparatus reduces monitoring costs, and increases monitoring accuracy.

The following description of the present invention with reference to the accompanying drawings will make other objectives and advantages of the present invention obvious, and can provide a comprehensive understanding of the present invention.

DESCRIPTION OF THE ACCOMPANYING DRAWINGS

DETAILED DESCRIPTION

Figure 1:
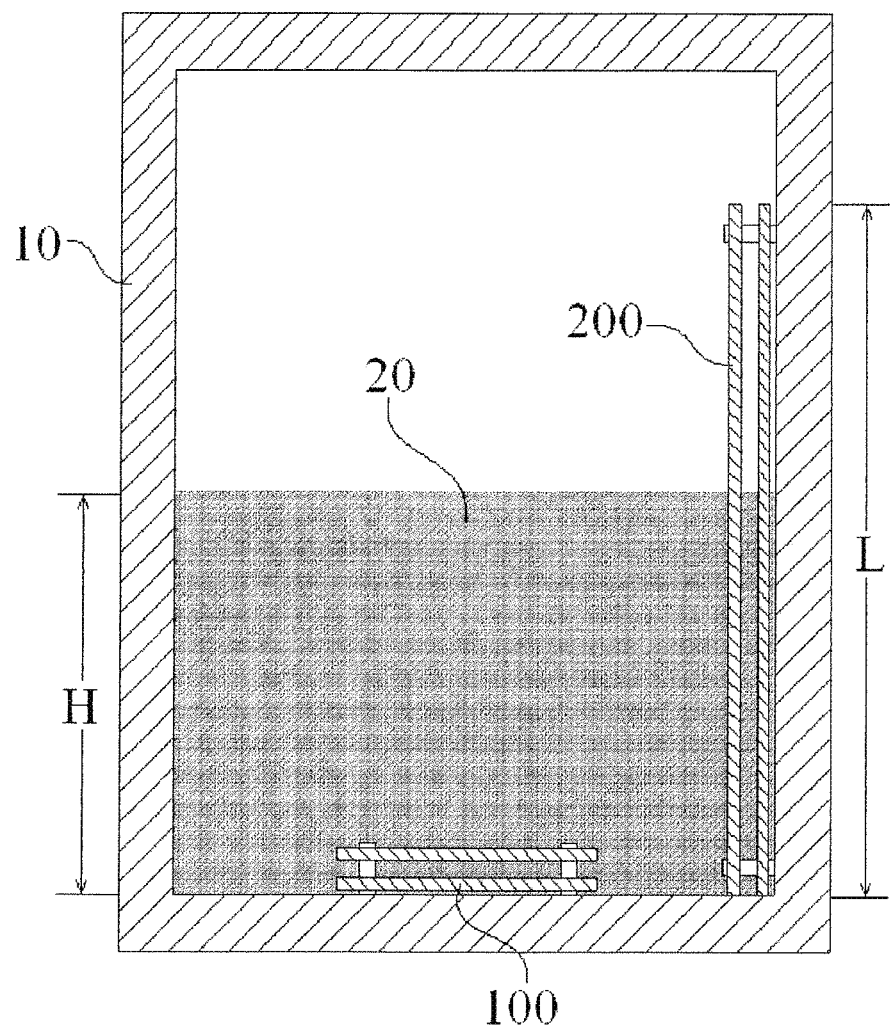
FIG. 1 shows a schematic sectional view of a compressor according to an embodiment of the present invention, wherein a first capacitance detector and a second capacitance detector are shown.

The technical solution of the present invention is further explained in detail below according to embodiments, with reference to the accompanying drawings. In the description, identical or similar reference signs indicate identical or similar components. The following explanation of embodiments of the present invention with reference to the accompanying drawings is intended to explain the overall inventive concept of the present invention, and should not be interpreted as a limitation of the present invention.

Furthermore, in the following detailed description, to facilitate explanation, several specific details are expounded to provide a comprehensive understanding of embodiments of the present disclosure. However, it is obvious that one or more embodiments could also be implemented in the absence of these specific details. In other cases, well-known structures and apparatuses are embodied as illustrations in order to simplify the accompanying drawings.

As stated above, to ensure that a compressor can operate safely, the quality of lubricating oil in the compressor must be monitored on-line in real time. According to an overall technical concept of the present invention, a monitoring apparatus is provided, for monitoring lubricating oil in a compressor. The monitoring apparatus includes: a first capacitance detector, disposed in the compressor and completely immersed in lubricating oil in the compressor; a calculation unit, for calculating a relative dielectric constant $\varepsilon_r$ of the lubricating oil in the compressor according to a first capacitance value $C_{11}$ detected by the first capacitance detector; and a determining unit, for monitoring whether the quality of the lubricating oil in the compressor is abnormal according to the relative dielectric constant $\varepsilon_r$ calculated.

In actual applications, operation safety of the compressor will be affected if the level of the lubricating oil in the compressor is too low. If the level of the lubricating oil in the compressor is too low, it will be impossible to provide a sufficient amount of lubricating oil to various components of the compressor, and as a result, the various components of the compressor will not be lubricated adequately. Consequently, it accelerates wear of the various components of the compressor, thereby shortening the service life of the compressor. Thus, once the level of the lubricating oil in the compressor is lower than a warning level, it is necessary to immediately switch off the compressor, and provide a sufficient amount of lubricating oil into the compressor.

Regarding on-line real-time monitoring of the level of lubricating oil in the compressor, in the conventional art, the level of lubricating oil in a compressor is generally monitored by a pressure-differential detector or a magnetic floating ball. However, since the pressure in the compressor is up to 45 bar, this will damage the pressure-differential detector or magnetic floating ball. Furthermore, since operating circumstance inside the compressor is very complex, for example, there will be foam, temperature instability, higher pressure fluctuation, and bigger density variation, it will make the pressure-differential detector or magnetic floating ball unable to precisely detect the level of the lubricating oil in the compressor.

In view of the above, the abovementioned monitoring apparatus further includes: a second capacitance detector, disposed vertically in the compressor. The calculation unit calculates, based on the calculated relative dielectric constant $\varepsilon_r$ of the lubricating oil in the compressor and a second capacitance value $C_{21}$ detected by the second capacitance detector disposed vertically in the compressor, a depth H to which the second capacitance detector is immersed in the lubricating oil in the compressor; the determining unit, monitors, based on the depth H calculated, whether the level of the lubricating oil in the compressor is lower than a safe level value.

According to a technical concept of the present invention, a monitoring method is provided, for monitoring lubricating oil in a compressor. The monitoring method includes steps of: calculating a relative dielectric constant $\varepsilon_r$ of the lubricating oil in the compressor according to a first capacitance value $C_{11}$ detected by a first capacitance detector completely immersed in the compressor, and monitoring whether quality of the lubricating oil in the compressor is abnormal according to the relative dielectric constant $\varepsilon_r$ calculated.

According to another technical concept of the present invention, the abovementioned monitoring method further includes the step of: calculating, based on a second capacitance value $C_{21}$ detected by a second capacitance detector disposed vertically in the compressor and the calculated relative dielectric constant $\varepsilon_r$ of the lubricating oil in the compressor, a depth H to which the second capacitance detector is immersed in the lubricating oil in the compressor, and monitoring, based on the depth H calculated, whether the level of lubricating oil in the compressor is lower than a safe level value.

FIG. 1 shows a schematic sectional view of a compressor according to an embodiment of the present invention, wherein a first capacitance detector 100 and a second capacitance detector 200 are shown.

In an embodiment of the present invention, a monitoring apparatus for monitoring lubricating oil 20 in a compressor 10 is disclosed. As FIG. 1 shows, in the embodiment illustrated, the monitoring apparatus mainly includes a first capacitance detector 100, a second capacitance detector 200, a calculation unit (not shown) and a determining unit (not shown).

As FIG. 1 shows, in an embodiment of the present invention, the first capacitance detector 100 is disposed in the compressor 10, and is completely immersed in the lubricating oil 20 in the compressor 10. Thus, the calculation unit of the monitoring apparatus can calculate a relative dielectric constant $\varepsilon_r$ of the lubricating oil 20 in the compressor 10 according to a first capacitance value $C_{11}$ detected by the first capacitance detector 100. The relative dielectric constant $\varepsilon_r$ of the lubricating oil 20 in the compressor 10 can be calculated according to formula (1):

$$\varepsilon_r = \frac{C_{11}}{C_{10}}, \quad (1)$$

wherein $C_{10}$ is a capacitance value detected by the first capacitance detector 100 in vacuum.

In the embodiments of the present invention, the determining unit of the monitoring apparatus monitors whether the quality of the lubricating oil 20 in the compressor 10 is abnormal according to the relative dielectric constant $\varepsilon_r$ calculated.

A brief description is given below of the principles of monitoring whether the quality of the lubricating oil 20 in the compressor 10 is abnormal according to the relative dielectric constant $\varepsilon_r$ calculated.

Generally, indices associated with the quality of lubricating oil in a compressor include dilution of the lubricating oil, foreign substance mixed into the lubricating oil, oxidation or carbonization of the lubricating oil, etc.

If the dilution of the lubricating oil in a compressor is too high, i.e. an excessive amount of coolant mixes into the lubricating oil in the compressor, the concentration of the lubricating oil in the compressor will be too low as a result. This will cause a reduction in the viscosity of the lubricating oil; once the viscosity of the lubricating oil is reduced, it will result in serious wear to the bearings of the compressor.

The relative dielectric constant of coolant is far greater than the relative dielectric constant of pure lubricating oil. Thus, once an excessive amount of coolant has mixed into lubricating oil, the relative dielectric constant of the lubricating oil (or a mixture of lubricating oil and coolant) will be greatly increased, and as a result, the relative dielectric constant $\varepsilon_r$ of the lubricating oil mentioned above and detected on-line will be greater than a predetermined dielectric constant value (or a dielectric constant warning value). Once the relative dielectric constant $\varepsilon_r$ of the lubricating oil mentioned above and detected on-line is greater than the predetermined dielectric constant value, the monitoring apparatus gives an alarm, and immediately switches off the compressor or reduces the dilution of the lubricating oil. For example, some of the coolant mixed into the lubricating oil can be evaporated out by heating the lubricating oil, so as to reduce the dilution of the lubricating oil, thereby reducing the relative dielectric constant $\varepsilon_r$ of the lubricating oil to a value below the warning value.

If foreign substance mixes into the lubricating oil, for instance iron fragments that have fallen off compressor bearings become mixed into the lubricating oil, this will aggravate wear of compressor components. Since the relative dielectric constant of iron fragments is far greater than the relative dielectric constant of pure lubricating oil, the relative dielectric constant of the lubricating oil will be greatly increased once iron fragments have mixed into lubricating oil, and as a result, the relative dielectric constant $\varepsilon_r$ of the lubricating oil mentioned above and detected on-line will be greater than a predetermined dielectric constant value (or a dielectric constant warning value). Once the relative dielectric constant $\varepsilon_r$ of the lubricating oil mentioned above and detected on-line is greater than the warning value, the monitoring apparatus gives an alarm, and immediately switches off the compressor. Once the compressor is switched off, the iron fragments must be removed from the lubricating oil.

If lubricating oil is oxidized or carbonized, the lubricating oil will lose its lubricating function, and this will lead to rapid wear of the compressor. Once lubricating oil has been oxidized or carbonized, the relative dielectric constant $\varepsilon_r$ thereof will increase sharply, and as a result, the relative dielectric constant $\varepsilon_r$ of the lubricating oil mentioned above and detected on-line will be greater than a predetermined dielectric constant value (or a dielectric constant warning value). Once the relative dielectric constant $\varepsilon_r$ of the lubricating oil mentioned above and detected on-line is greater than the warning value, the monitoring apparatus gives an alarm and immediately switches off the compressor. Once the compressor is switched off, the lubricating oil must be replaced with new lubricating oil.

As FIG. 1 shows, in the embodiment illustrated, the first capacitance detector 100 may be a parallel-plate capacitance detector, having a pair of parallel electrode plates facing each other.

Table 1 below shows a capacitance value detected when the first capacitance detector 100 shown in FIG. 1 is immersed in a certain pure fatty oil (the temperature of the fatty oil being 18° C.), and a relative dielectric constant of the fatty oil calculated on the basis of the detected capacitance value.

TABLE 1

| | No. | | | | | | | | | | Mean |
|---|---|---|---|---|---|---|---|---|---|---|---|
| | 1 | 2 | 3 | 4 | 5 | 6 | 7 | 8 | 9 | 10 | value |
| Capacitance value detected | 11.714 | 11.708 | 11.721 | 11.712 | 11.754 | 11.712 | 11.734 | 11.75 | 11.772 | 11.763 | 11.734 |
| Relative dielectric constant calculated | 3.1498 | 3.1729 | 3.1576 | 3.2017 | 3.1842 | 3.1628 | 3.15515 | 3.159 | 3.162 | 3.193 | 3.1708 |

According to Table 1 above, it can be clearly seen that the mean value of the relative dielectric constant of the pure fatty oil, detected by the parallel-plate first capacitance detector 100 provided in the present invention, is 3.1708. The true relative dielectric constant of the pure fatty oil is 3.20. As can be seen, the detection result of the first capacitance detector 100 mentioned above is substantially accurate, and the first capacitance detector 100 can be used to detect the relative dielectric constant of lubricating oil in the compressor.

Figure 2:
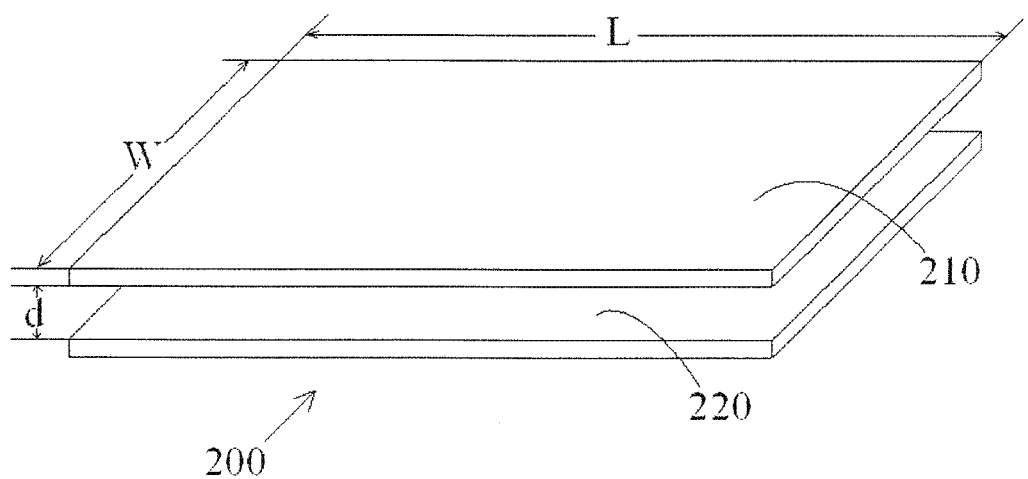
FIG. 2 shows a 3-D view of the second capacitance detector in FIG. 1.

FIG. 2 shows a schematic 3-D view of the second capacitance detector 200 in FIG. 1.

As shown in FIGS. 1 and 2, in the embodiment illustrated, both the first capacitance detector 100 and the second capacitance detector 200 are parallel-plate capacitance detectors. However, it should be noted that the present invention is not limited to the embodiment illustrated; the first capacitance detector 100 and the second capacitance detector 200 could also be capacitance detectors of any other type, e.g. cylindrical capacitance detectors.

As shown in FIGS. 1 and 2, in the embodiment illustrated, the second capacitance detector 200 has a pair of parallel electrode plates 210 and 220 facing each other. The length of the second capacitance detector 200 is L and the width of the second capacitance detector 200 is W, and the distance between the pair of electrode plates 210 and 220 is d.

As shown in FIGS. 1 and 2, in the embodiment illustrated, the second capacitance detector 200 is disposed in the compressor 10 vertically, and the depth to which the second capacitance detector 200 is immersed in the lubricating oil 20 in the compressor 10 is H, as shown in FIG. 1.

Thus, the calculation unit of the monitoring apparatus can calculate, based on the calculated relative dielectric constant $\varepsilon_r$ of the lubricating oil 20 in the compressor 10 and a second capacitance value $C_{21}$ detected by the second capacitance detector 200, the depth H to which the second capacitance detector 200 is immersed in the lubricating oil 20 in the compressor 10.

The depth H to which the second capacitance detector 200 is immersed in the lubricating oil 20 is calculated according to Formula (2):

$$H = \frac{L*(C_{21} - C_{20})}{(\varepsilon_r - 1)*C_{20}}, \quad (2)$$

wherein
$C_{20}$ is a capacitance value detected by the second capacitance detector 200 in air, and
L is the length of the second capacitance detector 200 in a vertical direction.

In the embodiments of the present invention, the determining unit of the monitoring apparatus monitors, based on the depth H calculated, whether the level of the lubricating oil 20 in the compressor 10 is lower than a safe level value.

Figure 3:
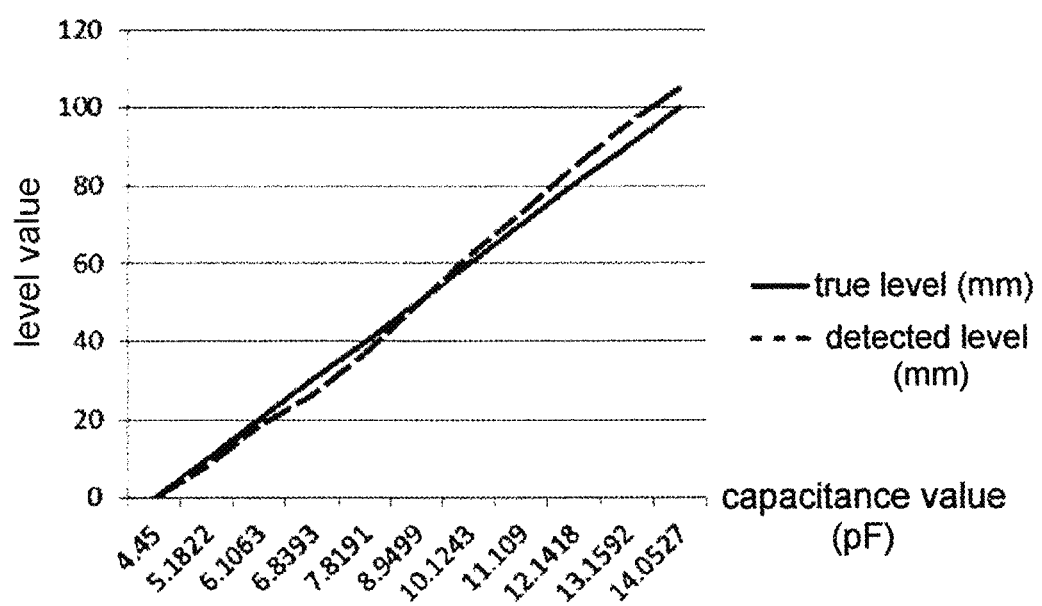
FIG. 3 shows a graph of a detected level of lubricating oil in a container, detected by the first capacitance detector and the second capacitance detector in FIG. 1, and a true level of the lubricating oil in the container.

FIG. 3 is a graph showing a detected level of certain fatty oil in a container, detected by using the first capacitance detector 100 and second capacitance detector 200 in FIG. 1, and a true level of fatty oil in the container.

As shown in FIG. 3, the x-axis indicates capacitance values detected by the second capacitance detector 200. The capacitance values detected by the second capacitance detector 200 increase as the level of fatty oil in the container rises.

As shown in FIG. 3, the y-axis indicates detected levels of the fatty oil in the container, calculated on the basis of the relative dielectric constants of the fatty oil, detected by the first capacitance detector 100, and capacitance values detected by the second capacitance detector 200.

As can be seen from FIG. 3, the difference between the detected level of the fatty oil in the container, detected by using the first capacitance detector 100 and the second capacitance detector 200 in FIG. 1, and the true level is very small, indicating that detection of the level of the fatty oil in the container by using the first capacitance detector 100 and the second capacitance detector 200 in FIG. 1 is accurate and reliable, so use for detecting the level of the lubricating oil 20 in the compressor 10 is entirely possible.

In an embodiment of the present invention, as shown in FIG. 1, the first capacitance detector 100 is substantially horizontally installed on a bottom wall of an oil tank in the compressor 10. Thus, it can be ensured that the first capacitance detector 100 is always completely immersed in the lubricating oil 20 in the compressor 10.

In an embodiment of the present invention, as shown in FIG. 1, the second capacitance detector 200 is vertically installed on a sidewall of the oil tank in the compressor 10. Thus, the second capacitance detector 200 can be vertically installed in the compressor 10 conveniently.

In an embodiment of the present invention, as shown in FIG. 1, a lower end face of the second capacitance detector 200 is in contact with a bottom wall of the oil tank in the compressor 10. Thus, the detected level H is equal to the level of lubricating oil 20 in the compressor 10. However, the present invention is not limited to the illustrated embodiment. The lower end face of the second capacitance detector 200 may be above the bottom wall of the oil tank in the compressor 10, and not be in contact with the bottom wall of the oil tank in the compressor 10. In this case, the sum of the detected level H and the gap distance between the lower end face of the second capacitance detector 200 and the bottom wall of the oil tank in the compressor 10 is equal to the level of the lubricating oil 20 in the compressor 10.

In the embodiment shown in FIG. 1, the first capacitance detector 100 and second capacitance detector 200 are two independent components which are separated physically. However, the present invention is not limited to the illustrated embodiment. The first capacitance detector 100 and second capacitance detector 200 may be integrated as a one-piece component.

In another embodiment of the present invention, a monitoring method is disclosed, for monitoring lubricating oil in a compressor. The monitoring method includes the following steps:

calculating a relative dielectric constant $\varepsilon_r$ of lubricating oil 20 in a compressor 10 according to a first capacitance value $C_{11}$ detected by a first capacitance detector 100, and monitoring whether quality of the lubricating oil 20 in the compressor 10 is abnormal according to the relative dielectric constant $\varepsilon_r$ calculated.

In an embodiment of the present invention, the monitoring method further includes:

calculating, based on the calculated relative dielectric constant $\varepsilon_r$ of the lubricating oil 20 in the compressor 10 and a second capacitance value $C_{21}$ detected by the second capacitance detector 200 disposed vertically in the compressor 10, a depth H to which the second capacitance detector 200 is immersed in the lubricating oil 20 in the compressor 10.

In another embodiment of the present invention, the abovementioned monitoring method may further include the step of: switching off the compressor 10 immediately when the calculated relative dielectric constant $\varepsilon_r$ is greater than a predetermined dielectric constant value or when the calculated depth H is less than a predetermined depth value.

As stated above, an important index associated with the quality of the lubricating oil in the compressor is dilution of the lubricating oil. If the dilution of the lubricating oil in the compressor is too high, i.e. an excessive amount of coolant is mixed into the lubricating oil in the compressor, the concentration of the lubricating oil in the compressor will be too low as a result. This will cause a reduction in the viscosity of the lubricating oil. Once the viscosity of the lubricating oil is reduced, it will result in serious wear to the bearings of the compressor. Thus, once the dilution of the lubricating oil is higher than a warning level, it is necessary to immediately switch off the compressor or reduce the dilution of the lubricating oil.

Thus, it is needed to monitor the dilution of the lubricating oil on-line in real time. The inventors of the present application, on the basis of a large amount of testing, have found that a certain functional relationship exists between the dilution of the lubricating oil and the relative dielectric constant of the lubricating oil. Thus, the dilution of the lubricating oil can be monitored by monitoring the relative dielectric constant of the lubricating oil.

Figure 4:
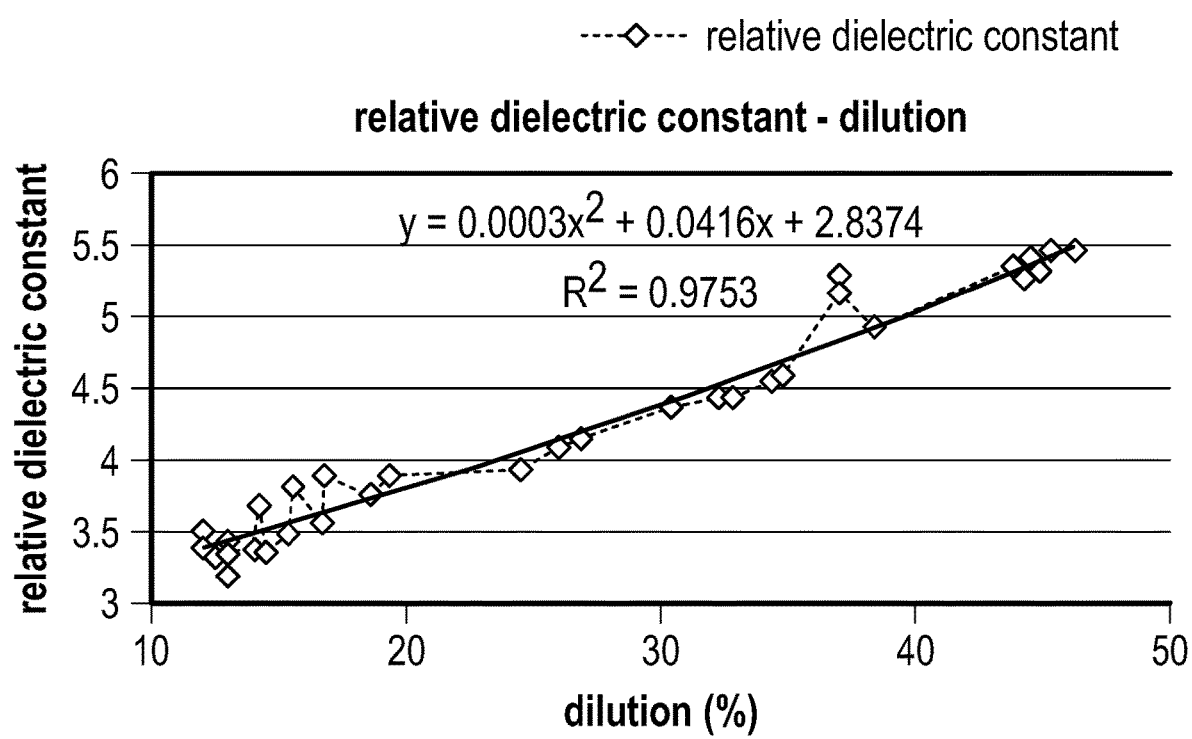
FIG. 4 shows a graph of relationship between dilution of the lubricating oil and relative dielectric constant of the lubricating oil.

FIG. 4 shows a graph of the relationship between the dilution of lubricating oil and the relative dielectric constant of lubricating oil.

As shown in FIG. 4, on the basis of a large amount of testing, the inventors of the present application have discovered relationship between the relative dielectric constant of lubricating oil and the dilution of lubricating oil under different operating conditions. The relationship therebetween may be expressed as the following functional relationship (x represents the dilution of the lubricating oil, y represents the relative dielectric constant of the lubricating oil):

$$y=0.0003x^2+0.0416x+2.8374 \quad (3)$$

wherein x ranges from 0% to 100%.

As can be seen from the relationship graph shown in FIG. 4, as the dilution x of lubricating oil increases, the relative dielectric constant value y of the lubricating oil also correspondingly rises. Thus, a warning value for the relative dielectric constant of the lubricating oil may be calculated according to a known warning value for the dilution of the lubricating oil (the maximum value permitted by normal operation) and the functional relationship (3). Once the relative dielectric constant of the lubricating oil is higher than the calculated warning value, it is necessary to immediately switch off the compressor or heat the lubricating oil to reduce the dilution of the lubricating oil.

However, the dilution of the lubricating oil is only one of parameters for judging the quality of the lubricating oil. During actual application, the quality of the lubricating oil in a compressor may also be monitored with reference to other parameters (such as viscosity, density or contaminants) of the lubricating oil, thereby determining a warning value for the relative dielectric constant. Thus, the relative dielectric constant of the lubricating oil may be measured, and the quality of the lubricating oil may be determined according to the relative dielectric constant and the warning value.

Those skilled in the art will understand that the embodiments described above are all demonstrative. Moreover, those skilled in the art could make improvements thereto. The structures described in the various embodiments may be freely combined, in the absence of any conflict in structures or principles.

Although the present invention has been explained with reference to the accompanying drawings, the embodiments disclosed in the accompanying drawings are intended to explain preferred embodiments of the present invention demonstratively, and must not be interpreted as a limitation of the present invention.

Although some embodiments of the present overall inventive concept have been displayed and explained, those skilled in the art will understand that changes may be made to these embodiments without departing from the principles and spirit of the present overall inventive concept. The scope of the present invention is defined by the claims and their equivalents.

It should be noted that the word "includes" does not exclude other elements or steps, and the word "a" does not exclude a plurality. Furthermore, no reference signs in the claims should be interpreted as limiting the scope of the present invention.

What is claimed is:

1. A monitoring apparatus, for monitoring lubricating oil in a compressor, wherein the monitoring apparatus comprises:
    a first capacitance detector, disposed in a compressor, and completely immersed in lubricating oil in the compressor, and operable for detecting a first capacitance value $C_{11}$;
    a calculation unit, for calculating a relative dielectric constant $\varepsilon_r$ of the lubricating oil in the compressor according to the first capacitance value $C_{11}$ detected by the first capacitance detector;
    a determining unit, for monitoring whether quality of the lubricating oil in the compressor is abnormal according to the relative dielectric constant $\varepsilon_r$ calculated; and
    a second capacitance detector, disposed vertically in the compressor,
    wherein
    the calculation unit calculates, based on the calculated relative dielectric constant $\varepsilon_r$ of the lubricating oil in the compressor and a second capacitance value $C_{21}$ detected by the second capacitance detector disposed vertically in the compressor, a depth H to which the second capacitance detector is immersed in the lubricating oil in the compressor.

2. The monitoring apparatus of claim 1, wherein:
    the first capacitance detector is a parallel-plate capacitance detector or a cylindrical capacitance detector;
    the second capacitance detector is a parallel-plate capacitance detector or a cylindrical capacitance detector.

3. The monitoring apparatus of claim 1, wherein:
    the first capacitance detector is substantially horizontally installed on a bottom wall of an oil tank in the compressor.

4. The monitoring apparatus of claim 1, wherein:
    the first capacitance detector and the second capacitance detector are two physically separated components or are integrated to form a one-piece component.

5. The monitoring apparatus of claim 1, wherein:
    the relative dielectric constant $\varepsilon_r$ of the lubricating oil in the compressor is calculated according to formula:

$$\varepsilon_r = \frac{C_{11}}{C_{10}},$$

wherein $C_{10}$ is a capacitance value detected by the first capacitance detector in vacuum.

6. The monitoring apparatus of claim 5, wherein:
    the depth H to which the second capacitance detector is immersed in the lubricating oil is calculated according to formula:

$$H = \frac{L*(C_{21}-C_{20})}{(\varepsilon_r-1)*C_{20}},$$

wherein
$C_{20}$ is a capacitance value detected by the second capacitance detector in air, and
L is the length of the second capacitance detector in a vertical direction.

7. The monitoring apparatus of claim 6, wherein:
the determining unit monitors whether the calculated relative dielectric constant $\varepsilon_r$ is greater than a predetermined dielectric constant value, and determines that the quality of the lubricating oil in the compressor is abnormal if the calculated relative dielectric constant $\varepsilon_r$ is greater than the predetermined dielectric constant value; and/or
the determining unit monitors whether the calculated depth H is less than a predetermined depth value, and determines that the level of the lubricating oil in the compressor is lower than a safe level value if the calculated depth H is less than the predetermined depth value.

8. The monitoring apparatus of claim 1, wherein:
the second capacitance detector is installed vertically on a sidewall of an oil tank in the compressor.

9. The monitoring apparatus of claim 8, wherein:
a lower end of the second capacitance detector is in contact with a bottom wall of the oil tank in the compressor.

10. A monitoring method, applicable for monitoring lubricating oil in a compressor, comprising steps of:
calculating a relative dielectric constant $\varepsilon_r$ of lubricating oil in a compressor according to a first capacitance value $C_{11}$ detected by a first capacitance detector immersed completely in the compressor, and monitoring whether quality of the lubricating oil in the compressor is abnormal according to the relative dielectric constant $\varepsilon_r$ calculated; and
calculating, based on a second capacitance value $C_{21}$ detected by a second capacitance detector disposed vertically in the compressor and the calculated relative dielectric constant $\varepsilon_r$ of the lubricating oil in the compressor, a depth H to which the second capacitance detector is immersed in the lubricating oil in the compressor.

11. The monitoring method of claim 10, further comprising:
switching off the compressor when the calculated relative dielectric constant $\varepsilon_r$ is greater than a predetermined dielectric constant value or when the calculated depth H is less than a predetermined depth value.

12. The monitoring method of claim 10, wherein:
the first capacitance detector is a parallel-plate capacitance detector or a cylindrical capacitance detector;
the second capacitance detector is a parallel-plate capacitance detector or a cylindrical capacitance detector.

13. The monitoring method of claim 10, wherein:
the first capacitance detector is substantially horizontally installed on a bottom wall of an oil tank in the compressor.

14. The monitoring method of claim 10, wherein:
the first capacitance detector and the second capacitance detector are two physically separated components or are integrated to form a one-piece component.

15. The monitoring method of claim 10, wherein:
the relative dielectric constant $\varepsilon_r$ of the lubricating oil in the compressor is calculated according to formula:

$$\varepsilon_r = \frac{C_{11}}{C_{10}},$$

wherein
$C_{10}$ is a capacitance value detected by the first capacitance detector in vacuum.

16. The monitoring method of claim 15, wherein:
the depth H to which the second capacitance detector is immersed in the lubricating oil is calculated according to formula:

$$H = \frac{L*(C_{21} - C_{20})}{(\varepsilon_r - 1)*C_{20}},$$

wherein
$C_{20}$ is a capacitance value detected by the second capacitance detector in air, and
L is the length of the second capacitance detector in a vertical direction.

17. The monitoring method of claim 16, wherein:
when the calculated relative dielectric constant $\varepsilon_r$ is greater than a predetermined dielectric constant value, the quality of the lubricating oil in the compressor is determined as abnormal; and/or
when the calculated depth H is less than a predetermined depth value, the level of the lubricating oil in the compressor is determined as lower than a safe level.

18. The monitoring method of claim 10, wherein:
the second capacitance detector is installed vertically on a sidewall of an oil tank in the compressor.

19. The monitoring method of claim 18, wherein:
a lower end of the second capacitance detector is in contact with a bottom wall of the oil tank in the compressor.

* * * * *